(12) United States Patent
Yamashita (10) Patent No.: US 10,987,002 B2
(45) Date of Patent: Apr. 27, 2021

(54) BIOLOGICAL INFORMATION MEASUREMENT DEVICE, AND BIOLOGICAL INFORMATION MEASUREMENT DEVICE OPERATING METHOD

(71) Applicant: OMRON HEALTHCARE Co., Ltd., Kyoto (JP)

(72) Inventor: Shingo Yamashita, Kyoto (JP)

(73) Assignee: OMRON HEALTHCARE Co., Ltd., Kyoto (JP)

(*) Notice: Subject to any disclaimer, the term of this patent is extended or adjusted under 35 U.S.C. 154(b) by 128 days.

(21) Appl. No.: 16/221,825

(22) Filed: Dec. 17, 2018

(65) Prior Publication Data

US 2019/0117081 A1   Apr. 25, 2019

Related U.S. Application Data

(63) Continuation of application No. PCT/JP2017/022720, filed on Jun. 20, 2017.

(30) Foreign Application Priority Data

Jun. 28, 2016 (JP) .............. JP2016-127591

(51) Int. Cl.
*G06F 1/32* (2019.01)
*A61B 5/02* (2006.01)
(Continued)

(52) U.S. Cl.
CPC .............. *A61B 5/02* (2013.01); *A61B 5/00* (2013.01); *A61B 5/746* (2013.01); *A61B 5/7445* (2013.01); *G06F 1/3203* (2013.01)

(58) Field of Classification Search
CPC .......... A61B 5/02; A61B 5/00; A61B 5/7445; A61B 5/746
(Continued)

(56) References Cited

U.S. PATENT DOCUMENTS 5,033,471 A   7/1991   Yokoe et al.
5,439,002 A   8/1995   Narimatsu et al.
(Continued)

FOREIGN PATENT DOCUMENTS

JP   S59-189829 A   10/1984
JP   H01-242031 A   9/1989
(Continued)

OTHER PUBLICATIONS

Search Report dated Jan. 23, 2020 in corresponding European Application No. 17819967.5; 8 pages.
(Continued)

*Primary Examiner* — Volvick Derose
(74) *Attorney, Agent, or Firm* — Maier & Maier, PLLC (57) ABSTRACT

A biological information measurement device operates using a battery as a power source, and enables the continuous measurement of biological information. The biological information measurement device is provided with: a battery charge level detection unit for detecting the charge level of the battery; a measurement control unit that ends measurement of biological information when the charge level of the battery falls below a threshold value during biological information measurement; and an information output unit that, when biological information measurement has been ended by the measurement control unit, outputs, to a display unit, information indicating the length of time over which biological information was measured.

8 Claims, 5 Drawing Sheets

(51) Int. Cl.
*A61B 5/00* (2006.01)
*G06F 1/3203* (2019.01)

(58) Field of Classification Search
USPC .......................................................... 713/320
See application file for complete search history.

(56) References Cited

U.S. PATENT DOCUMENTS

| | | | | |
|---|---|---|---|---|
| 5,563,495 | A * | 10/1996 | Tomiyori | H02J 7/008 |
| | | | | 320/153 |
| 6,778,934 | B1 * | 8/2004 | Hori | G05B 23/0216 |
| | | | | 702/119 |
| 2003/0169019 | A1 * | 9/2003 | Oosaki | H02J 7/0047 |
| | | | | 320/132 |
| 2008/0132225 | A1 * | 6/2008 | Ranta | H04J 11/0093 |
| | | | | 455/424 |
| 2010/0245102 | A1 * | 9/2010 | Yokoi | H01M 10/488 |
| | | | | 340/636.16 |
| 2012/0166240 | A1 * | 6/2012 | Jones | B60L 53/305 |
| | | | | 705/7.12 |
| 2013/0241626 | A1 * | 9/2013 | Bowling | H03K 5/00 |
| | | | | 327/407 |
| 2015/0157261 | A1 | 6/2015 | Sakagami | |
| 2016/0220134 | A1 * | 8/2016 | Inagaki | A61B 5/02427 |

FOREIGN PATENT DOCUMENTS

| | | |
|---|---|---|
| JP | H02-261421 A | 10/1990 |
| JP | H07-124130 A | 5/1995 |
| JP | 2004-230152 A | 8/2004 |
| JP | 2004230152 * | 8/2004 |
| JP | 2007-319233 A | 12/2007 |
| JP | 2007319233 * | 12/2007 |
| JP | 2013-085612 A | 5/2013 |
| WO | 01/93753 A1 | 12/2001 |
| WO | 2014/002388 A1 | 1/2014 |

OTHER PUBLICATIONS

International Search Report with English translation and Written Opinion dated Aug. 8, 2017 in corresponding International Application No. PCT/JP2017/022720; 8 pages.

* cited by examiner

BIOLOGICAL INFORMATION MEASUREMENT DEVICE, AND BIOLOGICAL INFORMATION MEASUREMENT DEVICE OPERATING METHOD

CROSS REFERENCE TO RELATED APPLICATIONS

This application is a continuation of PCT application No. PCT/JP2017/022720, which was filed on Jun. 20, 2017 based on Japanese Patent Application (No. 2016-127591) filed on Jun. 28, 2016, the contents of which are incorporated herein by reference.

BACKGROUND OF THE INVENTION

1. Field of the Invention

The present invention relates to a biological information measurement device, a biological information measurement device operating method, and a biological information measurement device operating program.

2. Description of the Related Art

In general, the biological information necessary for in vivo diagnosis such as blood pressure information, pulse information, heartbeat information and the like largely changes in the day. For this reason, the biological information is continuously measured and recorded from a measurement subject for diagnosis and the like.

As a device configured to continuously measure the biological information, a device configured to detect a pulse wave every one pulse (a time period for which the heart beats one time) and to calculate and store the biological information in a unit of one pulse based on the detected pulse wave has been known (refer to Patent Documents 1 to 3).

Patent Document 1: JP-A-H02-261421
Patent Document 2: JP-A-H07-124130
Patent Document 3: JP-A-H01-242031

SUMMARY OF THE INVENTION

A biological information measurement device of the present invention is a biological information measurement device configured to operate by using a battery as a power supply and capable of continuously measuring biological information, and includes a battery capacity detection unit configured to detect a capacity of the battery, a measurement control unit configured to, when the capacity falls below a threshold value during measurement of the biological information, end the measurement of the biological information, and an information output unit configured to, when the measurement of the biological information is ended by the measurement control unit, output information indicative of a time period for which the measurement of the biological information has been performed or information indicative of time at which the measurement of the biological information is ended.

A biological information measurement device operating method of the present invention is an operating method of a biological information measurement device configured to operate by using a battery as a power supply and capable of continuously measuring biological information, and includes a battery capacity detection step of detecting a capacity of the battery, a measurement control step of, when the capacity falls below a threshold value during measurement of the biological information, ending the measurement of the biological information, and an information output step of, when the measurement of the biological information is ended by the measurement control step, outputting information indicative of a time period for which the measurement of the biological information has been performed or information indicative of time at which the measurement of the biological information is ended.

A non-transitory computer-readable storage medium, which stores an biological information measurement device operating program of the present invention is an operating program of a biological information measurement device configured to operate by using a battery as a power supply and capable of continuously measuring biological information, and is configured to enable a computer of the biological information measurement device to execute a battery capacity detection step of detecting a capacity of the battery, a measurement control step of, when the capacity falls below a threshold value during measurement of the biological information, ending the measurement of the biological information, and an information output step of, when the measurement of the biological information is ended by the measurement control step, outputting information indicative of a time period for which the measurement of the biological information has been performed or information indicative of time at which the measurement of the biological information is ended.

DETAILED DESCRIPTION OF THE EXEMPLARY EMBODIMENTS

The biological information measurement device configured to continuously measure the biological information is used with being worn on a body of the measurement subject for a long time. For this reason, when the biological information measurement device is a battery-driven type to be driven by a battery, a time period for which the biological information can be measured is determined by a battery capacity upon start of the measurement.

For example, a case where the measurement subject wears the battery-driven biological information measurement device immediately before the sleep so as to monitor a change in the biological information during the sleep is assumed. In this case, when the battery capacity upon start of biological information measurement is not sufficient, the biological information cannot be measured at a point of time much earlier than the wake-up of the measurement subject, so that it is not possible to measure a sufficient amount of the biological information.

Although the battery of the biological information measurement device is preferably fully charged all the time, it is not convenient to fully charge the battery all the time. Patent Documents 1 to 3 do not consider the situations that are to occur when driving the device with the battery.

The present invention has been made in view of the above situations, and an object thereof is to provide a biological information measurement device, a biological information measurement device operating method, and a biological information measurement device operating program enabling determination on charging or replacement timing of a battery and capable of supporting measurement of a sufficient amount of biological information.

Hereinafter, an illustrative embodiment of the present invention will be described with reference to the drawings.

Figure 1:
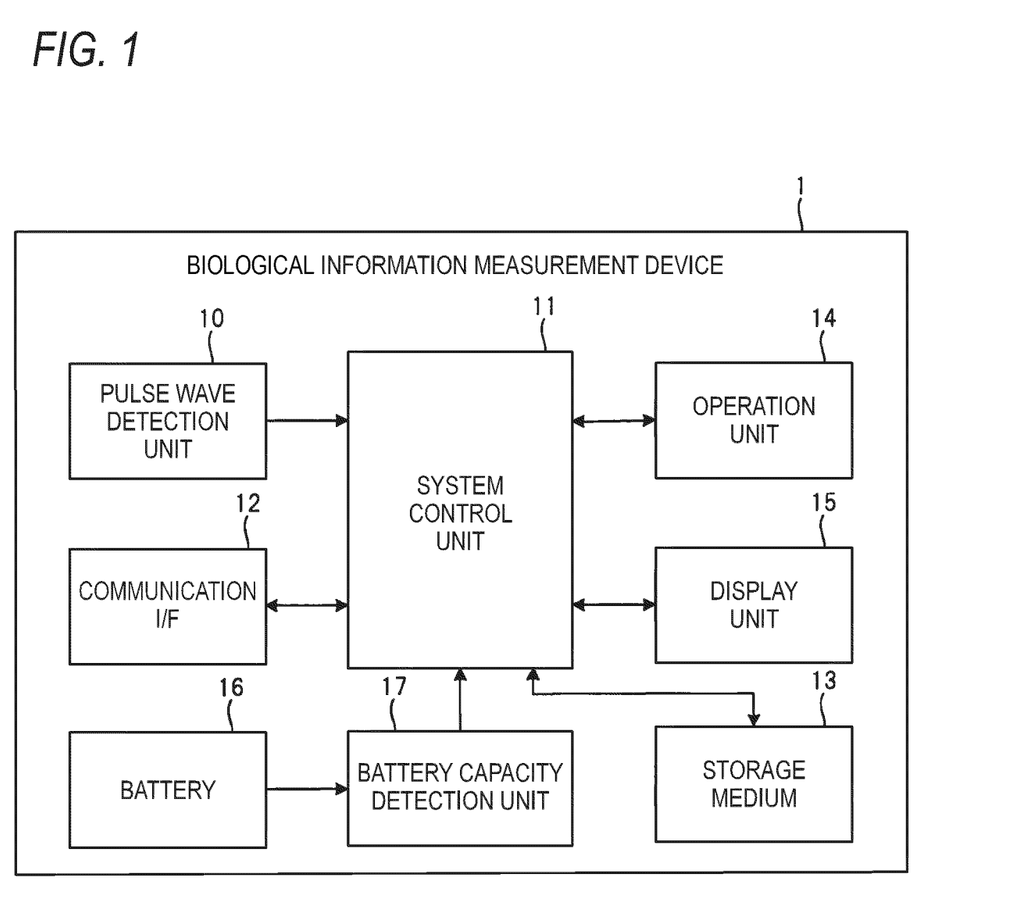
FIG. 1 depicts an internal hardware configuration of a biological information measurement device 1 for illustrating an illustrative embodiment of the present invention.

FIG. 1 depicts an internal hardware configuration of a biological information measurement device 1 for illustrating an illustrative embodiment of the present invention. The biological information measurement device 1 is used to monitor bedtime biological information of a measurement subject, for example.

The biological information measurement device 1 is to measure and store biological information such as blood pressure information, pulse information, vascular property information, heartbeat information and the like in a storage medium 13. The blood pressure information includes, for example a systolic arterial pressure, a diastolic pressure, an average blood pressure and the like. The pulse information includes, for example, a pulse rate and the like. The heartbeat information includes, for example, a heart rate and the like. The vascular property information includes, for example, AI (Augmentation Index), PTT (Pulse Transit Time) and the like.

The biological information measurement device 1 includes a pulse wave detection unit 10, a system control unit 11 configured to collectively control the entire device, a communication interface (I/F) 12, a storage medium 13, an operation unit 14, a display unit 15, a battery 16 and a battery capacity detection unit 17.

The pulse wave detection unit 10 is configured to detect a pulse wave to occur every one pulse from a living body part (for example, a wrist) of the measurement subject and to input the detected pulse wave in the system control unit 11. The pulse wave detection unit 10 is configured to detect a pressure pulse wave as the pulse wave by a tonometry method, for example. The pulse wave detection unit 10 may be configured to detect a volume pulse wave as the pulse wave. The pulse wave detection unit 10 may be configured to detect the pulse wave by reflected light from the artery obtained by irradiating light to the artery.

When the wave detection unit 10 is configured to detect the pulse wave by the tonometry method, the pulse wave detection unit 10 includes a pressure sensor and a pressing part such as an air bag configured to press the pressure sensor to a body surface. The pulse wave detection unit 10 is configured to detect the pulse wave based on a signal that is to be detected by the pressure sensor in a state where the pressure sensor is pressed to the body surface with a predetermined pressing force by the pressing part.

The system control unit 11 includes a processor, as a main body, and a ROM (Read Only Memory) in which a program and the like to be executed by the processor are stored, a RAM (Random Access Memory) as a work memory, and the like. The ROM configures a non-transitory storage medium from which a computer can read the program.

The communication I/F 12 is an interface for wired or wireless connection with other electronic devices (for example, a smart phone carried by the measurement subject wearing the biological information measurement device 1).

In the storage medium 13, a variety of data such as the biological information calculated by the system control unit 11 is stored. The storage medium 13 is configured by a flash memory, a hard disk and the like, for example. The storage medium 13 may be a portable type to be detachably mounted to the biological information measurement device 1.

The operation unit 14 is an interface for inputting an instruction signal to the system control unit 11, and is configured by buttons, a touch panel and the like for instructing start or end of diverse operations including measurement of the biological information.

The display unit 15 is to display a variety of information such as the measured biological information, and is configured by a liquid crystal display device, electronic paper or the like, for example.

The battery 16 configures a power supply of the biological information measurement device 1. Each of the hardware of the biological information measurement device 1 operates by power that is to be fed from the battery 16.

As the battery 16, any battery that can be used as a power supply of the electronic device can be used. For example, a primary battery such as an alkaline battery, a fuel battery using methanol fuel or the like, a secondary chargeable battery such as a lithium ion battery, and the like may be used.

The battery capacity detection unit 17 is configured to detect a capacity of the battery 16 and to notify information of the detected capacity to the system control unit 11.

Figure 2:
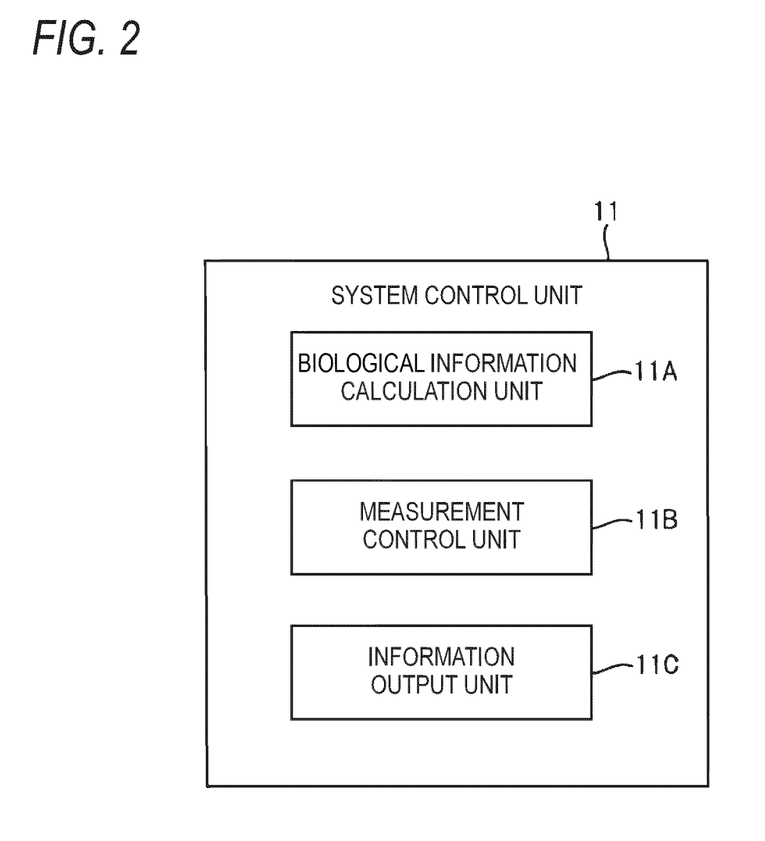
FIG. 2 is a functional block diagram of a system control unit 11 of the biological information measurement device 1 shown in FIG. 1.

FIG. 2 is a functional block diagram of the system control unit 11 of the biological information measurement device 1 shown in FIG. 1.

The system control unit 11 includes a biological information calculation unit 11A, a measurement control unit 11B and an information output unit 11C.

The biological information calculation unit 11A, the measurement control unit 11B and the information output unit 11C are configured as the processor (computer) executes the programs stored in the ROM.

The programs include a biological information measurement device operating program. The operating program is stored in the ROM during the manufacturing of the biological information measurement device 1 but may be stored in the ROM through a portable storage medium such as a memory card by a user or may be stored in the ROM by the user downloading the same via a network.

The biological information calculation unit 11A is configured to calculate the biological information based on the pulse wave input from the pulse wave detection unit 10 by the well-known method. The biological information calculation unit 11A uses the pulse wave detected every one pulse, as the pulse wave of a calculation target of the biological information, but may set a pulse wave detected every other pulse or every multiple pulses, as the calculation target of the biological information.

The biological information calculation unit 11A is configured to store the calculated biological information in the storage medium 13. Thereby, in the storage medium 13, the biological information in a unit of one pulse is accumulatively stored.

The measurement control unit 11B stops the pulse wave detection unit 10 to end the calculation (measurement) of the biological information when the capacity of the battery 16 notified from the battery capacity detection unit 17 falls below a threshold value.

As the threshold value, a value obtained by adding a value at which the biological information measurement device 1 can keep a dormant state to a value necessary for an operation of the pulse wave detection unit 10 and calculation of the biological information is set, for example.

The dormant state indicates a state in which the biological information cannot be measured but an operation of the operation unit 14 can be detected and a screen can be displayed on the display unit 15 by the system control unit 11.

When the measurement of the biological information is ended by measurement control unit 11B, the information output unit 11C outputs measurement time period information, which indicates a time period for which the measurement of the biological information has been performed, to the display unit 15.

Figure 3:
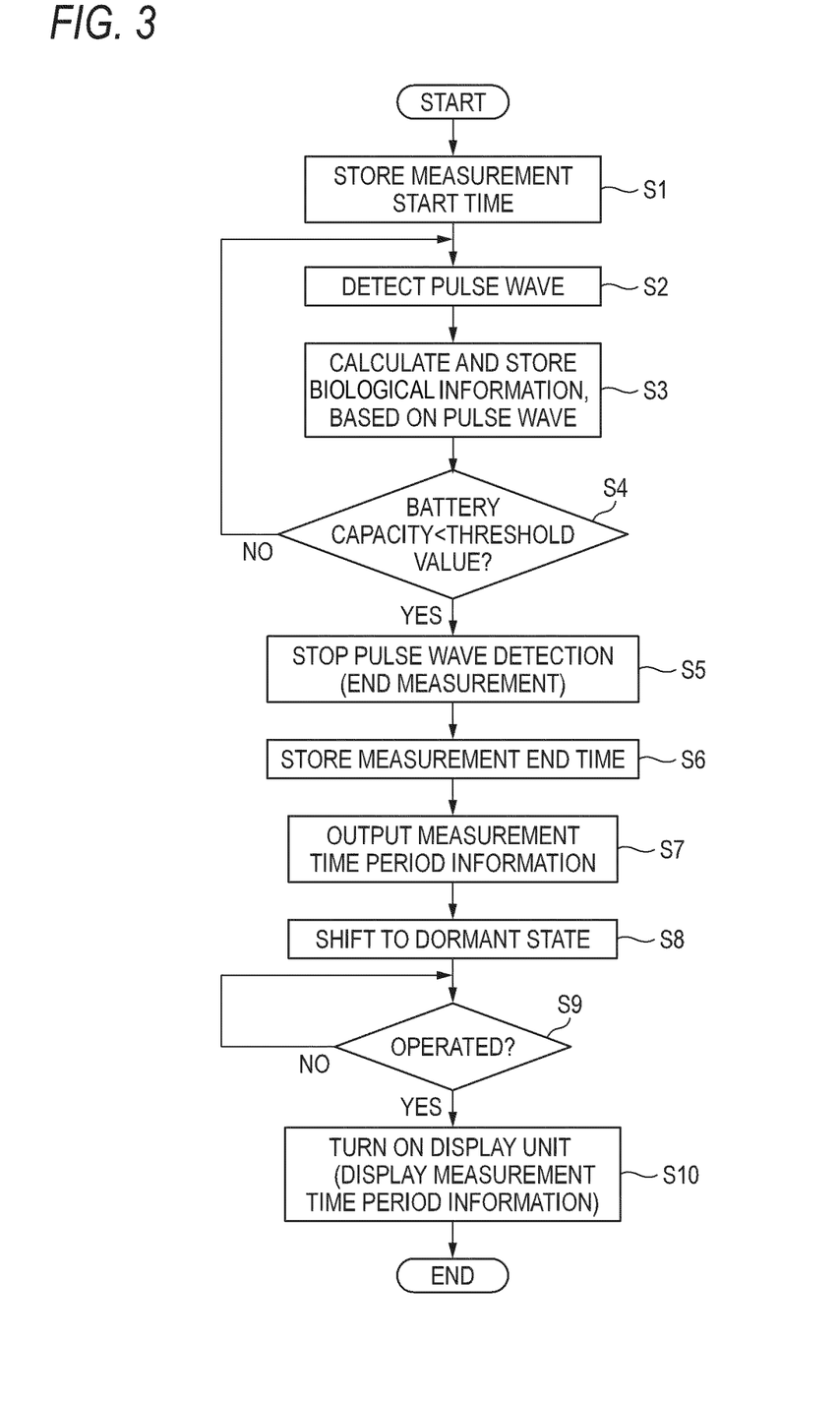
FIG. 3 is a flowchart depicting operations of the biological information measurement device 1 shown in FIG. 1.

FIG. 3 is a flowchart depicting operations of the biological information measurement device 1 shown in FIG. 1.

When the operation unit 14 is operated to input a measurement start instruction of the biological information to the system control unit 11, the information output unit 11C stores, as measurement start time, time at which the instruction signal has been received in the storage medium 13 (step S1), and activates the pulse wave detection unit 10 to start detection of the pulse wave.

When the pulse wave is detected by the pulse wave detection unit 10 (step S2), the biological information calculation unit 11A calculates the biological information based on the pulse wave, and stores the calculated biological information in the storage medium 13 (step S3).

After step S3, the measurement control unit 11B determines whether the capacity of the battery 16 falls below the threshold value (step S4).

When the capacity of the battery 16 is equal to or larger than the threshold value (step S4: NO), the processing returns to step S2 and the measurement of the biological information continues.

In the meantime, when a state in which the operation unit 14 is not operated continues for a predetermined time period during the measurement time period of the biological information started in accordance with the measurement start instruction, the system control unit 11 turns off the screen display of the display unit 15 for saving the power consumption.

When the capacity of the battery 16 falls below the threshold value (step S4: YES), the measurement control unit 11B stops the pulse wave detection unit 10 to end the measurement of the biological information (step S5).

Thereafter, the information output unit 11C stores, as measurement end time of the biological information, current time in the storage medium 13 (step S6).

Then, the information output unit 11C generates measurement time period information, which indicates a time period for which the measurement of the biological information has been performed, based on the information indicative of the measurement start time stored in the storage medium 13 and the information indicative of the measurement end time stored in the storage medium 13, and outputs the measurement time period information to the display unit 15 (step S7). The measurement time period information output to the display unit 15 is stored in an internal memory of the display unit 15.

Specifically, the information output unit 11C generates, as the measurement time period information, time information for displaying a time from the measurement start time to the measurement end time. Alternatively, the information output unit 11C generates, as the measurement time period information, start and end time information for displaying the measurement start time and the measurement end time.

After step S7, the system control unit 11 shifts the biological information measurement device 1 to the dormant state (step S8).

When the operation unit 14 is operated in the dormant state (step S9: YES), the system control unit 11 detects the operation, and turns on the screen display of the display unit 15. Thereby, the measurement time period information stored in the internal memory and an icon indicating the capacity of the battery 16 stored in advance in the internal memory are displayed on the display unit 15 (step S10).

In the meantime, the system control unit 11 may execute the processing of step S8 after generating the measurement time period information in step S7, and output the generated measurement time period information to the display unit 15 and display the measurement time period information on the display unit 15 when a determination result in step S9 is YES.

Figure 4:
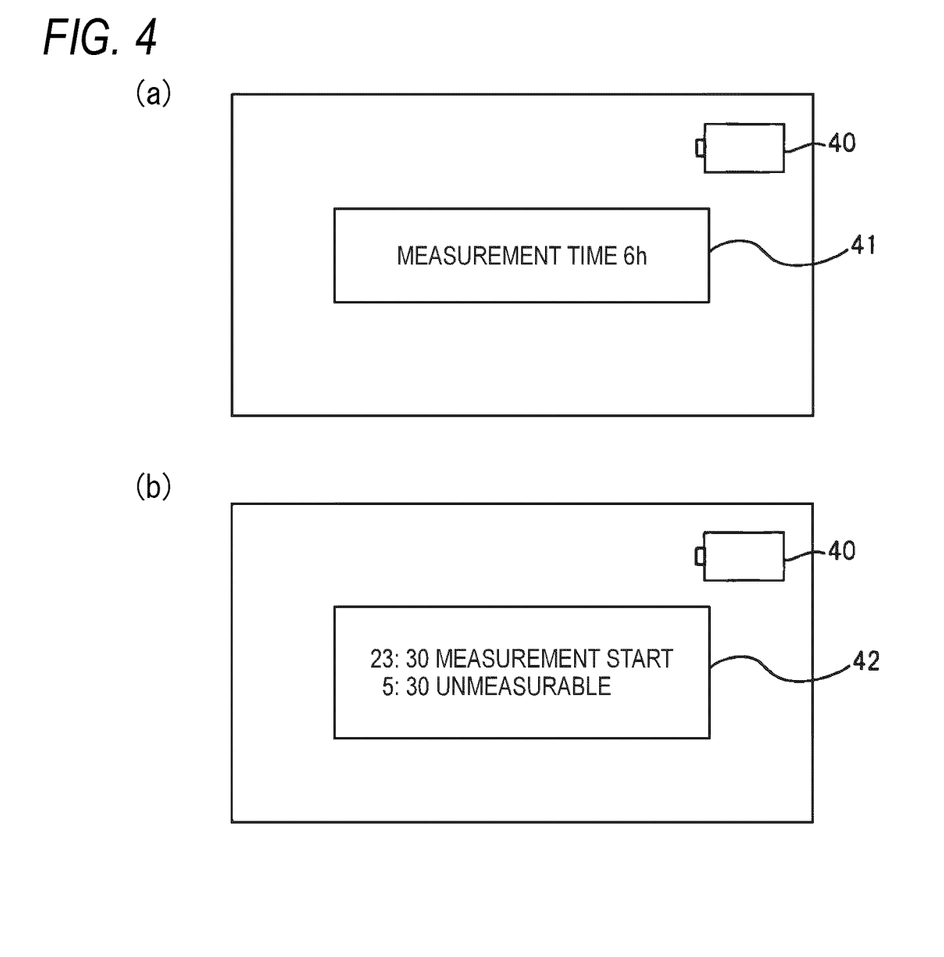
FIG. 4 depicts an example of a screen that is to be displayed on a display unit 15 of the biological information measurement device 1 shown in FIG. 1.

FIG. 4 depicts a screen example that is to be displayed on the display unit 15 of the biological information measurement device 1 shown in FIG. 1.

In the screen of (a) of FIG. 4, an icon 40 indicating that the capacity of the battery 16 is too low to measure the biological information and an image 41 based on the measurement time period information are included. The image 41 is a character image indicating that a time period between the measurement start time and the measurement end time is 6 hours (6 h).

In the screen of (b) of FIG. 4, the icon 40 and an image 42 based on the measurement time period information are included. The image 42 is a character image indicating that the measurement start time is 23:30 and time at which the capacity of the battery 16 fell below the threshold value and the biological information could not be thus measured is 5:30.

Like this, according to the biological information measurement device 1, when the capacity of the battery 16 falls below the threshold value and the biological information cannot be thus measured, the measurement time period information is generated, so that the measurement time period information can be checked through the display unit 15.

For example, a case where the measurement subject uses the biological information measurement device 1 during the sleep is assumed. In this case, even when the measurement of the biological information is ended on the way due to the capacity shortage of the battery 16, the measurement subject can know how long the measurement of the biological information was performed by seeing the screen of FIG. 4 displayed on the display unit 15 after the wake-up.

The measurement subject can know the capacity of the battery 16 by the icon displayed on the display unit 15 when starting the measurement of the biological information. When the measurement subject memorizes the corresponding capacity and sees the screen shown in FIG. 4 after the wake-up, the measurement subject can know how to adjust the capacity of the battery and the bedtime or wake-up time so as to prevent the biological information from being unmeasurable during the sleep.

Like this, according to the biological information measurement device 1, it is possible to enable the measurement subject to be aware of an action for preventing the measurement of the biological information from being impossible during a time period (for example, during the sleep) for which it is necessary to measure the biological information.

In the above, the information output unit 10C generates and outputs the measurement time period information to the display unit 15, in step S7. In a modified embodiment, when the measurement of the biological information is ended by the measurement control unit 11B, the information output unit 10C may output information, which indicates time at which the measurement of the biological information is ended, to the display unit 15.

That is, in step S7 of FIG. 3, the information output unit 10C may output the information indicative of the measurement end time stored in the storage medium 13 to the display unit 15. In this configuration, the processing of step S1 is not necessarily required.

Figure 5:
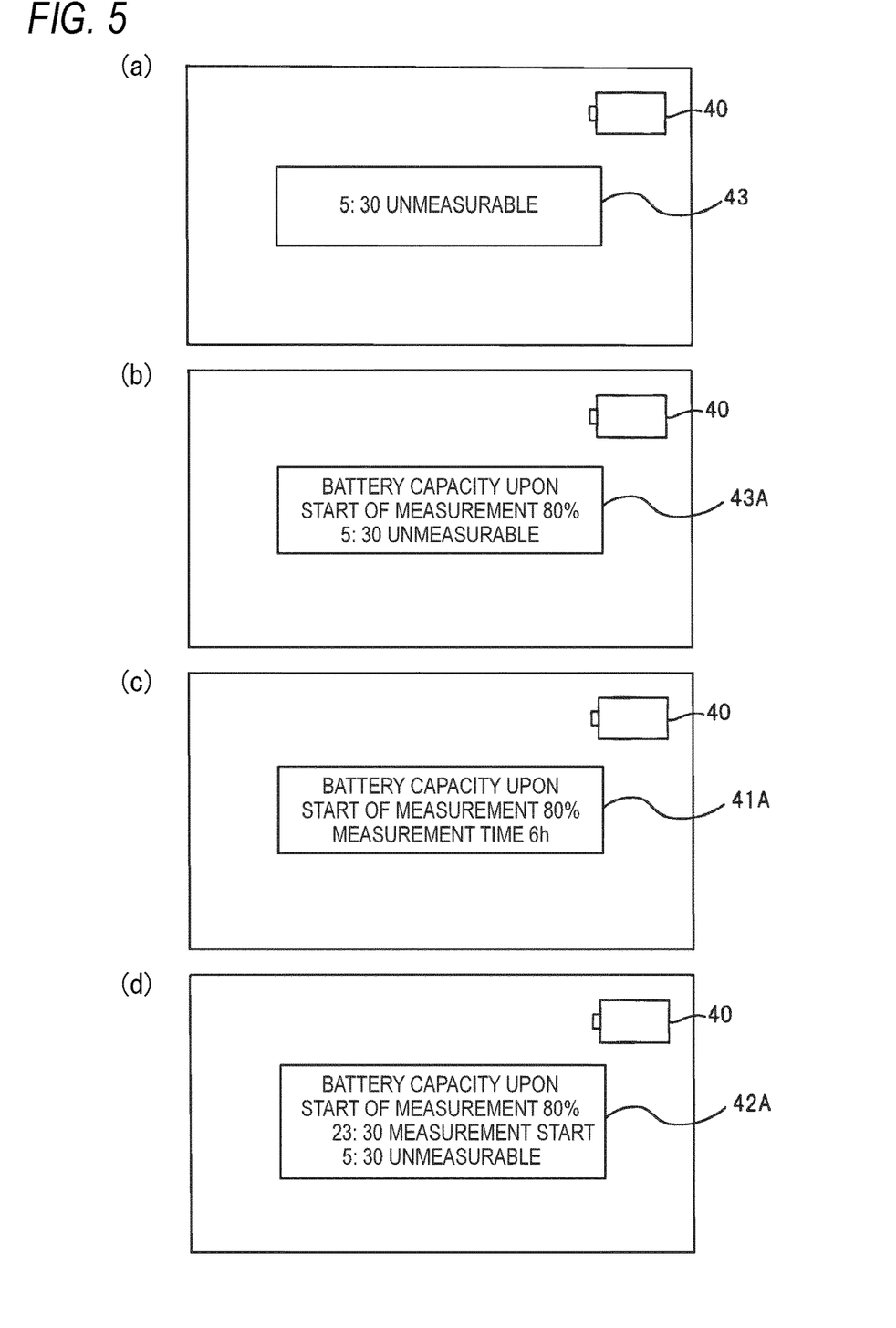
FIG. 5 depicts a modified embodiment of the screen that is to be displayed on the display unit 15 of the biological information measurement device 1 shown in FIG. 1.

In the configuration, a screen that is displayed on the display unit 15 in step S10 is as shown in (a) of FIG. 5, for example. In the screen of (a) of FIG. 5, the icon 40 and an image 43 based on the information indicative of the measurement end time are included. The image 43 is a character image indicating that the unmeasurable time (measurement end time) is 5:30.

Like this, even with the configuration in which the measurement end time can be displayed when the capacity of the battery 16 falls below the threshold value, when the measurement subject memorizes the capacity of the battery 16 upon the start of the measurement and the measurement start time, the measurement subject can know how to adjust the capacity of the battery and the bedtime or wake-up time.

The information output unit 10C may store, in the storage medium 13, the capacity of the battery 16 upon receiving of the measurement start instruction of the biological information (hereinafter, referred to as 'capacity upon start of the measurement'), and may further output information indicative of the capacity upon start of the measurement to the display unit 15 when the measurement of the biological information is ended by the measurement control unit 11B.

That is, in step S1 of FIG. 3, the information output unit 10C stores the capacity upon start of the measurement in the storage medium 13, in addition to the measurement start time, and in step S7 of FIG. 3, outputs the information indicative of the capacity upon start of the measurement to the display unit 15, in addition to the measurement time period information.

In this configuration, the screen that is displayed on the display unit 15 in step S10 is as shown in (b) of FIG. 5, (c) of FIG. 5 or (d) of FIG. 5, for example.

In the screen of (b) of FIG. 5, the icon 40 and a character image 43A indicating the measurement end time and the capacity upon start of the measurement are included.

In the screen of (c) of FIG. 5, the icon 40 and a character image 41A indicating the measurement time and the capacity upon start of the measurement are included.

In the screen of (d) of FIG. 5, the icon 40 and a character image 42A indicating the measurement start time, the measurement end time and the capacity upon start of the measurement are included.

Like this, the capacity upon start of the measurement can be checked with the display unit 15, so that even when the measurement subject does not memorize the capacity of the battery 16 upon start of the measurement, the measurement subject can take necessary actions, which improve the convenience.

In the meantime, after shifting to the dormant state, when the capacity of the battery 16 is further lowered to be below a minimum value of the capacity with which the dormant state can be kept, the system control unit 11 turns off the power supply of the biological information measurement device 1. Thereafter, when the battery 16 is charged and the power supply of the biological information measurement device 1 becomes on, the system control unit 11 may turn on the screen display of the display unit 15 to display the measurement time period information or both the measurement time period information and the capacity upon start of the measurement on the display unit 15.

According to the above configuration, even when the capacity of the battery 16 is lowered to a level at which the power supply of the biological information measurement device 1 becomes off, it is possible to immediately check the measurement time period information and the like at activation timing of the biological information measurement device 1, so that the convenience is improved.

Also, after the power supply of the biological information measurement device 1 is turned off, as described above, when charging of the battery 16 of the biological information measurement device 1 is started, the system control unit 11 may turn on the screen display of the display unit 15 to display the measurement time period information or both the measurement time period information and the capacity upon start of the measurement on the display unit 15. According to this configuration, it is possible to check the measurement time period information and the like at timing of the charging start, so that the convenience is improved.

When the data of the sets of the measurement start time, the measurement end time and the capacity upon start of the measurement corresponding to a plurality of days is stored in the storage medium 13, the system control unit 11 may estimate and calculate time at which the measurement of the biological information will be impossible, at a point of time at which the measurement start instruction of the biological information is issued, based on the data of the plurality of days and the time of the point of time, and may display the calculated time on the display unit 15, as wake-up suggestion time.

Thereby, the measurement subject can take actions to charge the battery 16, to set the wake-up time to the wake-up suggestion time and the like, without particular considerations.

In the above, the screen of FIG. 4 or 5 is displayed on the display unit 15 of the biological information measurement device 1. However, the screen may be displayed on a display unit of an electronic device capable of performing communication with the biological information measurement device 1.

For example, when the measurement of the biological information is ended by the measurement control unit 11B, the information output unit 10C transmits (outputs) the measurement time period information or the information indicative of the measurement end time from the communication I/F 12 to a smart phone carried by the measurement subject, and turns off the power supply of the biological information measurement device 1.

The smart phone is set to a state in which the smart phone can perform communication with the biological information measurement device 1 by a function of an installed application program. Also, the smart phone generates a screen for displaying the measurement time period information or the information indicative of the measurement end time received from the biological information measurement device 1, and displays the screen on the display unit by the function when a request is issued from the user.

Thereby, it is possible to check the screen of FIG. 4 or 5 on the display unit of the smart phone, so that the measurement subject can take a necessary action.

According to the above configuration, since the power for detecting an operation of the operation unit 14 and the power for operating the display unit 15 can be used for the measurement of the biological information, it is possible to prolong the measurable time of the biological information.

The disclosed illustrative embodiments are exemplary in every respect and should not be construed as being limited. The scope of the present invention is defined in the claims, not in the above description, and includes all changes within the meaning and scope equivalent to the claims.

For example, a configuration where the characters shown in FIG. 4 or 5 are read and notified to the measurement subject by a voice may also be possible. That is, the information output unit 10C may be configured to output the measurement time period information, the information indicative of the capacity upon start of the measurement and the like to a sound output unit such as a speaker.

As described above, the specification discloses following items.

(1) A biological information measurement device configured to operate by using a battery as a power supply and capable of continuously measuring biological information, the biological information measurement device including a battery capacity detection unit configured to detect a capacity of the battery, a measurement control unit configured to, when the capacity falls below a threshold value during measurement of the biological information, end the measurement of the biological information, and an information output unit configured to, when the measurement of the biological information is ended by the measurement control unit, output information indicative of a time period for which the measurement of the biological information has been performed or information indicative of time at which the measurement of the biological information is ended.

(2) The biological information measurement device according to the above (1), wherein when the measurement of the biological information is ended by the measurement control unit, the information output unit further outputs information indicative of a capacity of the battery upon start of the measurement of the biological information.

(3) The biological information measurement device according to the above (1) or (2), further including a display unit, wherein the information output unit is configured to output the information to the display unit to display the information on the display unit.

(4) The biological information measurement device according to the above (3), wherein when the measurement of the biological information is ended by the measurement control unit, the biological information measurement device shifts to a dormant state, and the display unit displays the information when an operation is performed in the dormant state.

(5) The biological information measurement device according to the above (3) or (4), wherein when a power supply of the biological information measurement device is turned on after that the measurement of the biological information is ended by the measurement control unit and the power supply of the biological information measurement device is turned off, the display unit displays the information.

(6) The biological information measurement device according to the above (3) or (4), wherein when charging of the battery is started after that the measurement of the biological information is ended by the measurement control unit and a power supply of the biological information measurement device is turned off, the display unit displays the information.

(7) An operating method of a biological information measurement device configured to operate by using a battery as a power supply and capable of continuously measuring biological information, the operating method including a battery capacity detection step of detecting a capacity of the battery, a measurement control step of, when the capacity falls below a threshold value during measurement of the biological information, ending the measurement of the biological information, and an information output step of, when the measurement of the biological information is ended by the measurement control step, outputting information indicative of a time period for which the measurement of the biological information has been performed or information indicative of time at which the measurement of the biological information is ended.

(8) A non-transitory computer-readable storage medium, which stores an operating program of a biological information measurement device configured to operate by using a battery as a power supply and capable of continuously measuring biological information, the operating program being configured to enable a computer of the biological information measurement device to execute a measurement control step of, when a capacity of the battery falls below a threshold value during measurement of the biological information, ending the measurement of the biological information, and an information output step of, when the measurement of the biological information is ended by the measurement control step, outputting information indicative of a time period for which the measurement of the biological information has been performed or information indicative of time at which the measurement of the biological information is ended.

The present invention can be conveniently and effectively used for a portable blood pressure meter, particularly.

According to the present invention, it is possible to provide the biological information measurement device, the biological information measurement device operating method, and the biological information measurement device operating program enabling determination on charging or replacement timing of the battery and capable of supporting measurement of the sufficient amount of the biological information.

Although the present invention has been described with reference to the specific illustrative embodiment, the present invention is not limited to the illustrative embodiments and can be diversely changed without departing from the disclosed technical spirit of the present invention.

What is claimed is:

1. A biological information measurement device configured to operate by using a battery as a power supply and capable of continuously measuring biological information, the biological information measurement device comprising:
   a battery capacity detection unit configured to detect a capacity of the battery;
   a measurement control unit configured to, when the capacity falls below a threshold value during measurement of the biological information, end the measurement of the biological information; and
   an information output unit configured to, when the measurement of the biological information is ended by the measurement control unit, output information indicative of a time period for which the measurement of the biological information has been performed or information indicative of time at which the measurement of the biological information is ended;

wherein the time period is the difference between the starting time of the measurement and the ending time of the measurement.

2. The biological information measurement device according to claim 1,
wherein when the measurement of the biological information is ended by the measurement control unit, the information output unit further outputs information indicative of a capacity of the battery upon start of the measurement of the biological information.

3. The biological information measurement device according to claim 1, further comprising a display unit,
wherein the information output unit is configured to output the information to the display unit to display the information on the display unit.

4. The biological information measurement device according to claim 3,
wherein when the measurement of the biological information is ended by the measurement control unit, the biological information measurement device shifts to a dormant state, and
wherein the display unit displays the information when an operation is performed in the dormant state.

5. The biological information measurement device according to claim 3,
wherein when a power supply of the biological information measurement device is turned on after that the measurement of the biological information is ended by the measurement control unit and the power supply of the biometric information measurement device is turned off, the display unit displays the information.

6. The biological information measurement device according to claim 3,
wherein when charging of the battery is started after that the measurement of the biological information is ended by the measurement control unit and a power supply of the biological information measurement device is turned off, the display unit displays the information.

7. An operating method of a biological information measurement device configured to operate by using a battery as a power supply and capable of continuously measuring biological information, the operating method comprising:
a battery capacity detection step of detecting a capacity of the battery;
a measurement control step of, when the capacity falls below a threshold value during measurement of the biological information, ending the measurement of the biological information; and
an information output step of, when the measurement of the biological information is ended by the measurement control step, outputting information indicative of a time period for which the measurement of the biological information has been performed or information indicative of time at which the measurement of the biological information is ended;
wherein the time period is the difference between the starting time of the measurement and the ending time of the measurement.

8. A non-transitory computer-readable storage medium, which stores an operating program of a biological information measurement device configured to operate by using a battery as a power supply and capable of continuously measuring biological information, the operating program being configured to enable a computer of the biological information measurement device to execute:
a measurement control step of, when a capacity of the battery falls below a threshold value during measurement of the biological information, ending the measurement of the biological information; and
an information output step of, when the measurement of the biological information is ended by the measurement control step, outputting information indicative of a time period for which the measurement of the biological information has been performed or information indicative of time at which the measurement of the biological information is ended;
wherein the time period is the difference between the starting time of the measurement and the ending time of the measurement.

* * * * *